(12) United States Patent
Mazur et al.

(10) Patent No.: US 6,867,235 B2
(45) Date of Patent: Mar. 15, 2005

(54) HELIANTHRONE DERIVATIVES AS ANTI-CANCER AGENTS

(75) Inventors: Yehuda Mazur, Tel Aviv (IL); Gad Lavie, Rehovot (IL)

(73) Assignees: Yeda Research and Development Co. Ltd., Rehovot (IL); New York University, New York, NY (US)

( * ) Notice: Subject to any disclaimer, the term of this patent is extended or adjusted under 35 U.S.C. 154(b) by 0 days.

(21) Appl. No.: 10/209,427

(22) Filed: Jul. 30, 2002

(65) Prior Publication Data

US 2003/0105357 A1 Jun. 5, 2003

Related U.S. Application Data

(63) Continuation of application No. PCT/IL01/00091, filed on Jan. 31, 2001, which is a continuation-in-part of application No. 09/494,296, filed on Jan. 31, 2000, now Pat. No. 6,229,048.

(51) Int. Cl.[7] ...................... A61K 31/195; A61K 31/12
(52) U.S. Cl. ........................ 514/565; 514/680
(58) Field of Search .................. 514/565, 680

(56) References Cited

U.S. PATENT DOCUMENTS 6,229,048 B1 * 5/2001 Mazur et al. .............. 564/300

FOREIGN PATENT DOCUMENTS

| EP | 599307 | * | 6/1994 |
| WO | WO 97/04761 | | 2/1997 |
| WO | WO 99/06347 | | 2/1999 |

OTHER PUBLICATIONS

G. Lavie et al., XP-000995892 "A photodynamic pathway to apoptosis and necrosis induced by dimethyl tetrahydroxy-helianthrone and hypericin in leukemic cells: possible relevance to photodynamic therapy" Br. J. Cancer, vol. 79 (3/4) pp. 423–432 (1999).

Wei Zhang et al., XP-000995885, "Malignant Glioma Sensitivity to Radiotherapy, High-dose Tamoxifen, and Hypericin: Corroborating Clinical Response in Vitro: Case Report" Neurosurgery, vol. 38, No. 3, pp. 587–591 (1996).

Vandenbogaerde et al., XP-000996307, "Cytotoxicity and antiproliferative effect of Hypericin and derivatives after photosensitization", Photochemistry and Photobiology, vol. 67, No. 1 pp. 119–125 (1998).

Kimura et al., XP000996204, "Hypericin inhibits choroidal endothelial cell proliferation and cored formation in vitro", Current Eye Research vol. 16, No. 10, pp 967–972 (1997).

Showalter et al., XP000996205, "Small molecule inhibitors of the platelet-derived growth factor receptor, and Src family tyrosine kinases", Pharmacology and Therapeutics, vol. 76, No. 1–3, pp. 55–71 (1997).

Couldwell et al., XP000996206, :Hypercin: A potential antiglioma therapy, Neurosurgery, vol. 35, No. 4, pp. 705–710, (1994).

* cited by examiner

*Primary Examiner*—Alton N. Pryor
(74) *Attorney, Agent, or Firm*—Winston & Strawn LLP

(57) ABSTRACT

Hypericin, helianthrone and derivatives thereof of general formula (I)

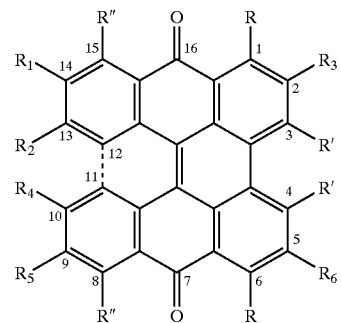

wherein the dotted line between positions 11 and 12 represent an optional C11–C12 bond; R is independently selected from the group consisting of hydroxy, $C_1$–$C_{10}$ alkoxy, NH—$C_1$–$C_{10}$ alkyl, and NH-hydroxy($C_1$–$C_{10}$)alkyl; R' is independently selected from the group consisting of hydroxy and $C_1$–$C_{10}$ alkoxy; R" is independently selected from the group consisting of hydrogen, hydroxy, $C_1$–$C_{10}$ alkoxy, NH—$C_1$–$C_{10}$ alkyl, and NH-hydroxy($C_1$–$C_{10}$)alkyl; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl, provided that R" is not hydrogen when there is a C11–C12 bond, are useful as inhibitors of angiogenesis and can be used to prevent formation of metastases and restenosis and for the treatment of angiogenesis-associated ophthalmologic disorders. In addition, the helianthrones of formula (I) can be used for the treatment of tumors in the absence of light irradiation. New compounds include those of formula I which are other than hypericin and known hypericin derivatives and there is either a C11–C12 bond or at least one R" is other than hydrogen.

13 Claims, 10 Drawing Sheets

HELIANTHRONE DERIVATIVES AS ANTI-CANCER AGENTS

CROSS-REFERENCE TO RELATED APPLICATIONS

This application is a continuation of the U.S. National Stage designation of International Application PCT/IL01/00091, filed Jan. 31, 2001, the entire content of which is expressly incorporated herein by reference thereto, which is a continuation-in-part of application Ser. No. 09/494,296 filed Jan. 31, 2000, now U.S. Pat. No. 6,229,048.

FIELD OF THE INVENTION

The present invention relates to the therapeutic use of polycyclic dianthraquinones such as hyperycins and helianthrones as inhibitors of angiogenesis, and to the use of some of them, particularly of 1,3,4,6-tetrahydroxy-helianthrone and derivatives thereof, as anti-cancer agents in the absence of light irradiation.

BACKGROUND OF THE INVENTION

The discovery of the signal transduction pathways that activate cell proliferation in response to interactions between growth factors and corresponding cellular receptors, triggered an extensive search for inhibitors that can interfere with this cascade in malignancies where malignant cells undergo uncontrolled proliferation. The chemical signals in this cascade have been identified as phosphorylation of proteins either on tyrosine residues, catalyzed by a group of enzymes collectively termed protein tyrosine kinases (PTK), or on serine/threonine residues by protein kinases A, B, and C. Protein kinase C (PKC) is also an important cellular signal transducer that contains a catalytic domain which phosphorylates substrates and a regulatory domain which controls its activity. Polyhydroxylated flavones such as genistein and quercetin were identified as inhibitors of the phosphorylation kinases (Losiewicz et al., 1994).

Perylene quinones are a unique group of kinase inhibitors (Diwu et al., 1994). The first of these compounds to be thoroughly evaluated was hypericin, a potent photodynamic agent initially discovered by the present inventors to be virucidal to retroviruses (Lavie et al., 1989; Meruelo et al., 1988), and subsequently to all lipid-enveloped viruses (Tang et al., 1990). Additional studies identified hypericin as a potent and irreversible light-dependent inhibitor of protein kinase C (PKC), particularly when PKC is translocated to the cell membrane following cell activation, this PKC inhibitory activity of hypericin being possibly related to its antiretroviral activity (Takahashi et al., 1989).

Hypericin is able to act within biological systems in the dark, possibly because of a low red/ox potential, and this appears to enable electron scavenging from physiological transfer reactions (Lavie et al., 1994). The unique combination of properties of hypericin prompted its current clinical evaluation in phase II clinical trials as an anti-tumor agent in the treatment of malignant glioma (Couldwell et al., 1994). This neoplasia relies on PKC signaling for cell proliferation. Hypericin is also a potent photosensitizer capable of generating singlet oxygen and free radicals (Hadjur et al., 1994). These properties also render it useful in photodynamic therapy (PDT) of superficial tumors accessible to light irradiation.

Unfortunately, hypericin is active in only half of the cases and, in addition, may cause severe side effects, such as prolonged post-treatment sensitivity to light, a condition medically known as hypericism. It would be desirable to provide additional photosensitizing agents and cell proliferation signal transduction inhibitors which can elicit their cytotoxic effect with greater efficiency as compared with existing agents and, potentially, with lower and less severe side effects.

The present inventors have disclosed previously that some helianthrone derivatives may be useful in photodynamic therapy (PDT) of tumors, to elicit destruction of tumors in conjunction with light irradiation (PCT Publication WO 99/06347).

While photodynamic properties have been implicated in the mechanism of the biological activities of hypericin, many of these activities also occur in the dark. Effects such as growth inhibition of malignant glioma cells are independent of light (Couldwell et al. 1994); the virucidal activity of hypericin, while strongly enhanced by light has also been documented in the dark against murine cytomegalovirus (Hudson et al., 1991)

Nowhere in the background art is it taught or suggested that perihydroxylated polycyclic dianthraquinones are useful for the inhibition of tumor metastases and prevention of angiogenesis. There is thus a widely recognized unmet need for inhibitors of angiogenesis which specifically blocks the proliferation of vascular structures, substantially without affecting other physiological processes, including inhibition of angiogenesis associated with tumor growth or progression, restenosis and ophthalmologic disorders.

SUMMARY OF THE INVENTION

The present invention is based on the surprising finding that some helianthrone deivatives are capable, at micromolar concentrations, of inhibiting transduction of signalsfor cell proliferation and cell progression through the cell replication cycle, indicating that they can be used as antineoplastic agents for the treatment of cancer in the absence of light irradiation.

It is further based on the surprising finding that hypericin and helianthrones interfere with the process of angiogenesis (formation of new blood vessels) both in the eye and in the formation of primary tumors and particularly metastases, indicating that they can be used for treatment of ophthalmologic disorders associated with angiogenesis and for treatment of primary tumors and prevention of formation of metastases.

It is thus an object of the present invention to provide pharmaceutical compositions comprising helianthrone and hypericin derivatives effective as inhibitors of angiogenesis and suitable for the treatment of angiogenesis-associated ophthalmologic disorders and for inhibition of formation of metastases and of restenosis. It is a further object of the present invention to provide such pharmaceutical compositions comprising such helianthrone derivatives effective as anti-cancer agents in the absence of light irradiation.

It is now disclosed that the compositions of the present invention comprising the helianthrone derivatives previously described in WO 99/06347 to act as anti-cancer agents in conjunction with light in photodynamic therapy, are unexpectedly effective as well in the absence of light irradiation. Furthermore, these compositions and also those containing hypericin, known for the treatment of primary tumors, or hypericin derivatives, are unexpectedly useful as anti-metastatic agents. The compositions of the present invention are now disclosed to possess hitherto unknown anti-angiogenic activity. This invention thus further relates to pharmaceutical compositions that are useful for the treatment of pathological angiogenesis or in conditions requiring inhibition of angiogenesis.

Hypericin and helianthrone and derivatives of both are now disclosed to interfere with the process of tumor angiogenesis. This discovery renders these compounds useful as treatment modalities in cancer patients undergoing surgical removal of primary tumors to prevent the growth of incurable metastases. Surgery has been established to stimulate the growth of micrometastases that were maintained dormant by growth factor inhibitors secreted from the primary tumors. These compounds may prevent metastatic growth by interfering with the production or activity of vascular endothelial growth factor (VEGF) or other angiogenic factors. VEGF, a potent enhancer of vascular permeability, is known to exert in vivo a key role in pathological neovascularization associated with many diseases including tumor neovascularization, rheumatoid arthritis, and diabetic retinopathy.

The present invention thus provides, in one aspect, the use of a compound selected from hypericin, helianthrone or derivatives thereof for the preparation of a pharmaceutical composition for inhibition of angiogenesis, said compound having the general formula (I):

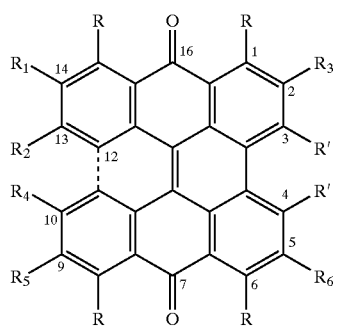

wherein the dotted line between positions 11 and 12 represent an optional C11–C12 bond; R is independently selected from the group consisting of hydroxy, $C_1$–$C_{10}$ alkoxy, NH—$C_1$–$C_{10}$ alkyl, and NH-hydroxy($C_1$–$C_{10}$)alkyl; R' is independently selected from the group consisting of hydroxy and $C_1$–$C_{10}$ alkoxy; R" is independently selected from the group consisting of hydrogen, hydroxy, $C_1$–$C_{10}$ alkoxy, NH—$C_1$–$C_{10}$ alkyl, and NH-hydroxy($C_1$–$C_{10}$)alkyl; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl, provided that R" is not hydrogen when there is a C11–C12 bond.

In the general formula (I), the helianthrone derivatives are those wherein there is no bond between positions 11 and 12 and R" is H at positions 8 and 15, and the hypericin derivatives are those wherein there is an additional ring formed by the bond between positions 11 and 12 and R" is not H at positions 8 and 15.

Examples of such compounds as the currently most preferred embodiments of the present invention are hypericin, 10,13-dimethyl-1,3,4,6-tetrahydroxyhelianthrone and 10,13-dimethyl-1,3,4,6-tetramethoxyhelianthrone of formulas A, B and C as follows:

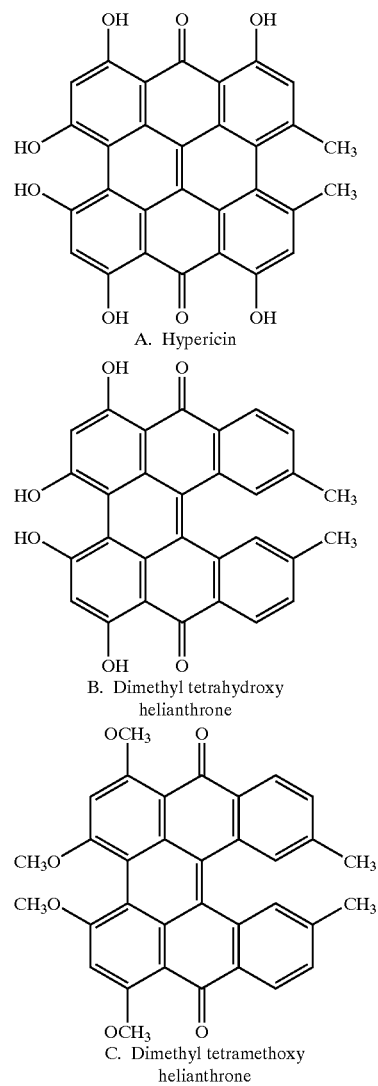

In one embodiment, the pharmaceutical composition comprising a compound of the general formula (I) is for use in the treatment of angiogenesis-associated ophthalmologic disorders such as, but not being limited to, retinopathies, including but not limited to diabetic, retinopathy, macular degeneration and eye, particularly bacterial, infections.

In another embodiment, the pharmaceutical composition comprising a compound of the general formula (I) is for use in the prevention of metastases.

In a further embodiment, the pharmaceutical composition comprising a compound of the general formula (I) is for use in the prevention of restenosis particularly after percutaneous transluminal coronary angioplasty.

In still a further embodiment, the pharmaceutical composition comprising a helianthrone compound of the formula (I) is useful for inhibiting transduction of cell proliferation signals and is thus suitable for the treatment of cancer in the absence of light irradiation.

In another aspect, the present invention provides pharmaceutical compositions comprising a compound of the general formula (I) as described above for the uses as described above.

In a further aspect, the present invention provides a method for the inhibition of angiogenesis which comprises administering to a patient in need thereof an effective amount of a compound of the general formula (I).

In still a further aspect, the present invention provides a method for inhibiting transduction of cell proliferation signals comprising administering to a patient in need thereof an effective amount of a helianthrone compound of the formula (I). In a preferred embodiment of this aspect, the helianthrone compound is useful for the treatment of cancer in the absence of light irradiation.

DETAILED DESCRIPTION OF THE INVENTION

Figure 1:
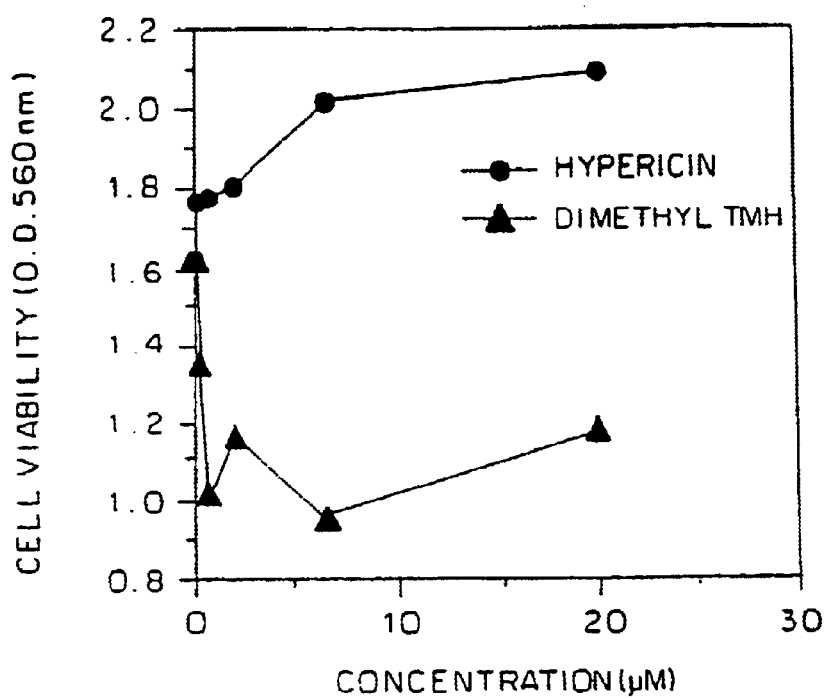
FIG. 1 shows the effects of various concentrations of 10,13-dimethyl-1,3,4,6-tetramethoxy-helianthrone (dimethyl TMH) and hypericin on U251 human glioblastoma cell viability in complete darkness.

The compositions according to the present invention are now disclosed to act as effective anti-cancer agents even in the absence of light. Furthermore, compositions according to the invention are now disclosed to be especially potent anti-metastatic agents. Unexpectedly, the compositions of the invention are now disclosed to be effective anti-angiogenic agents. Thus these compositions may be used in a variety of conditions and diseases involving pathological angiogenesis including but not limited to restenosis, angiogenesis-associated ophthalmological diseases and neovascularization associated with tumor formation and progression to metastases.

These hitherto unknown attributes were detected while studying the effects of hypericin and of helianthrone derivatives on breast adenocarcinoma tumors induced in mice with the DA-3$^{HI}$ cell line and on murine anaplastic squamous carcinoma tumors induced with the SQ-2 cell line. Both are highly metastatic tumors and if surgically resected after having reached a diameter larger than 5 mm, the mice will go on to develop metastases in the lungs and liver. The metastases cause death of the animals within approximately two months following surgery.

Although these two types of tumors are not inhibited by hypericin, it was unexpectedly discovered that if the tumors are removed surgically as the tumors reach a diameter of 8–10 mm, 2–4 injections of hypericin into the peritoneum protect the mice from death due to metastases. Hypericin prevents thus the development of metastases.

Furthermore, in trying to understand why primary tumors are less affected by hypericin whereas metastases are potently inhibited, it was unexpectedly discovered that hypericin and also 10,13-dimethyl-1,3,4,6-tetrahydroxyhelianthrone and its derivative 10,13-dimethyl-1,3,4,6-tetramethoxyhelianthrone prevented neovascularization (ability of the tumor to induce formation of new blood vessels to provide blood and nutrient supply to the growing tumors). By preventing development of new blood vessels to supply a growing metastasis, the rapidly growing metastatic focus is deprived of nutrients and oxygen for its rapidly multiplying cells and the lesion degenerates.

Thus it is now disclosed that hypericin itself and helianthrone as well as their derivatives are useful in the inhibition of pathological angiogenesis, including neovascularization associated with tumor progression or ophthalmologic disorders as well as endothelial cell proliferation associated with restenosis.

The mechanisms by which cancer cells induce the formation of novel blood vessels and direct them towards the tumor has been extensively investigated, and is known to involve complex mechanisms. The cancer cells secrete vascular endothelium growth factor (VEGF) that directs the growth of newly formed blood vessels in the direction of the VEGF concentration gradient towards the higher concentration of VEGF eventually reaching the tumor (Folkman J., 1985; Folkman J. et al., 1989).

In the compounds of formula (I) used in the present invention, R is selected from the group consisting of hydroxy, $C_1$–$C_{10}$ alkoxy, NH—$C_1$–$C_{10}$ alkyl, and NH-hydroxy($C_1$–$C_{10}$)alkyl; R' is selected from the group consisting of hydroxy and $C_1$–$C_{10}$ alkoxy; and $R_1$, $R_2$, $R_3$, $R_4$, and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl.

As used herein, "$C_1$–$C_{10}$ alkyl, "$C_1$–$C_{10}$ alkoxy" and "$C_1$–$C_{10}$ alkoxycarbonyl" refer to straight or branched radicals having 1 to 10 carbon atoms. Examples of such alkyl radicals are, without being limited to, methyl, ethyl, propyl, isopropyl, butyl, hexyl, and octyl Examples of such alkoxy radicals are, without being limited to, methoxy, ethoxy, propyloxy, isopropyloxy, butoxy, hexyloxy, and octyloxy. Examples of such alkoxycarbonyl radicals are, without being limited to, methoxycarbonyl, ethoxycarbonyl, propyloxycarbonyl. In one preferred embodiment, R, R' and $R_1$ to $R_6$ are methyl, but longer aliphatic chains envisaged in these positions instead of the methyl group may have advantages such as prolongation of biological activity due to better retention by cells and requiring less frequent administration.

Preferred compounds used in the invention are hypericin, helianthrone and derivatives thereof of formula (I) wherein the two Rs at positions 1 and 6 are hydroxy, methoxy, butylamino or hydroxyethylamino, the two R's at positions 3 and 4 are hydroxy or methoxycarbonyl, $R_2$ and $R_5$ at positions 14 and 9 are hydrogen, and $R_3$ and $R_6$ at positions 2 and 5 are hydrogen or bromo. Examples of such preferred compounds are 1,3,4,6-tetrahydroxyhelianthrone, 1,3,4,6-tetramethoxyhelianthrone, 10,13-dimethyl-1,3,4,6-tetrahydroxyhelianthrone, 10,13-di(methoxycarbonyl)-1,3,4,6-tetramethoxyheli-anthrone, 1,6-di-N-butylamino-3,4-dimethoxyhelianthrone, 1,6-di-N-butylamino-3,4-dimethoxy-10,13-dimethylhelianthrone, 1,6-di-(N-hydroxyethylamino)-3,4-dimethoxy-helianthrone, 2,5-dibromo-1,3,4,6-tetrahydroxyhelianthrone, 2,5-dibromo-10,13-dimethyl-1,3,4,6-tetrahydroxyhelianthrone, and, most preferably, 10,13-dimethyl-1,3,4,6-tetramethoxyhelianthrone.

The compounds of the formula (I) according to the invention in which $R_2$ and $R_4$ are each lower alkyl can be prepared by the method described in U.S. Pat. No. 5,120,412 using as a starting material a 1,3-dihydroxy-6-(lower alkyl)-anthraquinone of the formula (II):

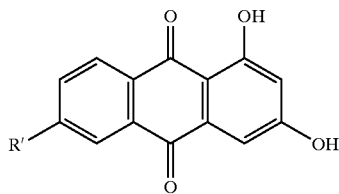

II in which R' is lower alkyl. Compound II is reduced to the corresponding anthrone of the formula (III)

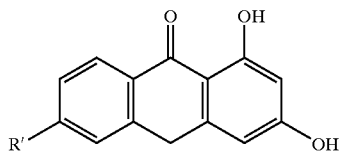

III in which R' is as defined above and compound III is condensed to obtain desired compounds of formula (I) in which R is lower alkoxy.

Other compounds of formula (I) can be prepared in an analogous manner using appropriately substituted 1,3-dihydroxy-anthraquinones.

The compounds of formula (I) in which $R_2$ and $R_4$ are each lower alkoxycarbonyl can be prepared from the diacetyl derivatives of the compound of formula (II) above in which R' is methyl, by oxidation with $CrO_3$ to form the compound of the formula (IV):

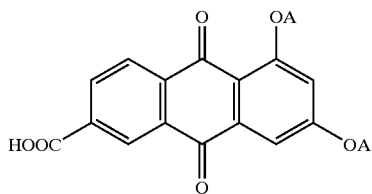

IV which is then dimerized by the method of Spitzner (*Angew. chem. Int. Ed.*, 16, 46 (1977)) to form a compound of formula (I) in which R is carboxy which is then esterified with lower alkanol to obtain the desired product of formula (I) in which $R_2$ and $R_4$ are lower alkoxycarbonyl.

The compounds of formula (I) in which each R at positions 1 and 6 is alkylamino or hydroxy alkylamino may be obtained by amination of the corresponding compound of Formula I, in which each R is alkoxy, with an alkyl amine such as butyl amine, or a hydroxyalkyl amine such as ethanolamine.

According to the present invention, compounds are provided which inhibit cell proliferation through the mitotic cycle. It was surprising to discover that these compounds, and particularly, 10,13-dimethyl-1,3,4,6-tetramethoxyhelianthrone (herein designated "dimethyl TMH"), are highly potent in deregulating several cell-cycle related checkpoints, which coordinate the orderly passage of cells through the different phases of the mitotic cycle. In this cycle, cells in G0 resting phase move into G1 protein and RNA accumulation phase. The cells then enter the S phase in which the genomic DNA is duplicated. As DNA duplication is completed, the cells are in the G2 phase with double the amount of DNA, ready for division, and progress into cell division M phase (mitosis), in which the cell divides into two daughter cells. Thus, dimethyl TMH was found to possess basic inhibitor activity of transduction of cell proliferation signals and to arrest malignant cells, including glioblastoma and neuroblastoma cells at mid S and G2 phases of the cell replication cycle. In mice bearing squamous cell carcinoma tumors, dimethyl TMH completely inhibited the spread of the tumor into multiple foci and the tumors hardened, became necrotic, and fell off after prolonged treatment.

In human malignant glioblastoma cell lines, the blockage of orderly advance of the cells through the different cycle phases culminated in cell death (FIG. 1), with dimethyl-TMH identified to be more potent than hypericin in killing the tumor cells in culture in complete darkness. Cell killing by dimethyl-TMH occurred at doses in which hypericin had no effect on the cultures. Surprisingly, dimethyl-TMH was equally more potent than hypericin in the photodynamic induction of cell death when treatments were performed in conjunction with light. The mechanisms that operate in the dark were very different from those that mediate light-induced photosensitization. In the dark, cell death occurs approximately four days after the compound is administered, whereas the cells died within 2–3 hours with light.

On normal human peripheral blood mononuclear cells, dimethyl-TMH had no effect on cell viability. Furthermore, intraperitoneal administration of the compound to BALB/c mice on a daily basis for one week had no adverse effect on the animals. In BALB/c mice bearing anaplastic squamous cell carcinoma tumors, treatments with 200 μg/mouse every other day resulted in significant inhibition of tumor growth compared to tumor bearing untreated control mice.

The pharmaceutical compositions of the invention will be administered to the patient by standard procedures. The amount of compound to be administered and the route of administration will be determined according to the kind of tumour, stage of the disease, age and health conditions of the patient. The preferable routes of administration are intravenous or direct injection into the solid tumor of the aqueous solution of the active compound comprising conventional pharmaceutically acceptable carriers and additives, and topical treatment of the skin tumors with suitable topical compositions. In disseminated tumors with metastases or systemic cancers such as leukemias and lymphomas, the preferential routes are systemic routes, the intravenous or the oral routes being preferred.

The compounds of the present invention can be used to treat various types of cancers and their metastases, including, but without being limited to, squamous cell carcinoma, basal cell carcinoma, melanoma, Kaposi sarcoma, breast carcinoma, prostate carcinoma, hemangioma, meningioma, astrocytoma, neuroblastoma, carcinoma of the pancreas, gastric carcinoma, colorectal carcinoma, colon carcinoma, transitional cell carcinoma of the bladder, and carcinoma of the larynx, chronic myeloid leukemia, acute lymphocytic leukemia, acute promyclocytic leukemia, multiple myelonia, T-cell lymphoma and B-cell lymphomas.

The compound used according to the invention can be formulated by any required method to provide pharmaceutical compositions suitable for administration to a patient.

The novel compositions contain, in addition to the active ingredient, conventional pharmaceutically acceptable carriers, diluents and the like. Solid compositions for oral administration, such as tablets, pills, capsules or the like, may be prepared by mixing the active ingredient with conventional, pharmaceutically acceptable ingredients such as corn starch, lactose, sucrose, sorbitol, talc, stearic acid, magnesium stearate, dicalcium phosphate and gums, with pharmaceutically acceptable diluents. The tablets or pills can be coated or otherwise compounded with pharmaceutically acceptable materials known in the art to provide a dosage form affording prolonged action or sustained release. Other solid compositions can be prepared as microscapsules for parenteral administration. Liquid forms may be prepared for oral administration or for injection, the term including subcutaneous, intramuscular, intravenous, and other parenteral routes of administration. The liquid compositions include aqueous solutions, with or without organic cosolvents, aqueous or oil suspensions, emulsions with edible oils, as well as similar pharmaceutical vehicles. In addition, the compositions of the present invention may be formed as encapsulated pellets or other depots, for sustained delivery.

The active dose for humans is generally in the range of from 0.1 micrograms to about 1 mg per kg body weight, in a regimen of one or more times a day. However, administration at longer intervals may also be possible, for compounds or formulations having prolonged action.

In general, the preferred range of dosage is from 1 to 200 micrograms per kg body weight. It is evident to one skilled in the art that dosage form and regimen would be determined by the attending physician, according to the disease to be treated, method of administration, and the patient's general condition. It will be appreciated that the most appropriate administration of the pharmaceutical compositions of the present invention will depend first and foremost on the clinical indication being treated. The prophylactic treatment of a healthy individual at high risk for pathological angiogenesis will necessitate a sustained maintenance dosage regimen sufficient to inhibit angiogenesis. This type of treatment might be applied to individuals at risk for diabetic retinopathy, retinopathy of prematurity, macular degeneration and other conditions that are known to afflict particular sets of patients. In contradistinction, the treatment of existing disease might require higher doses at more frequent intervals. It is further anticipated that the treatment of certain conditions known to involve abnormal vascular smooth muscle cell proliferation, including restenosis, will be treated beneficially with compositions according to the present invention in an amount sufficient to inhibit vascular smooth muscle cell proliferation.

It will be appreciated by the skilled artisan that in some instances treatments may beneficially include the administration of the compositions according to the present invention in conjunction with a depot or medical device. Thus, by way of example, the treatment of angoigenesis in the eye may necessitate an intraocular implant. Similarly, the treatment of restenosis associated endothelial cell proliferation may necessitate application of the composition in conjunction with angioplasty, e.g., as a coating on a stent or similar device.

EXAMPLES

The invention will now be illustrated by the following non-limiting Examples.

Experimental Procedures

A. Cell Lines

Human HL-60 leukemic cells were grown in RPMI-1640 supplemented with 15% fetal calf serum, 100 mM glutamine and 100 units/ml penicillin-streptomycin. Human erythroleukemia K-562 cells (derived from a chronic myeloid leukemia pateient) were grown in the same medium supplemented with 10% fetal calf serum. These cells and the human U251 glioblastoma, U87MG glioblastoma and LAN5 neuroblastoma cells used in the experiments are available from the ATCC. All cell lines were cultured in a humidified 5% $CO_2$/95% air atmosphere at 37° C.

B. Cell Viability

Cell viability was monitored by the MTT assay which measures reduction of 3-(4,5-dimethylthiazol-2-yl)-2,5-diphenyl tetrazolium bromide to formasan by mitochondria of viable cells as described in Mossman, T., *J. Immunogen.*, 21, 235–248 (1983). The cells are incubated with MTT for four hours at 37° C. and analyzed in an ELISA reader at 560 nm. The optical density of formasan generated by untreated cell cultures (O.D. control) is defined as one MTT unit. The number of MTT units in culture samples undergoing treatments is calculated as the ratio $(O.D._{sample} - O.D._{blank})/O.D._{control}$.

C. Photodynamic Stress

Photodynamic (PD) stress is the level of phototoxicity inflicted upon target cells by photodynamic compounds and exposure to light. Light irradiation was performed from a fluorescent source of two parallel 40 Watts tubes placed at a fixed distance of 16 cm and measured to emit an incidence of 4 mWatt/$cm^2$. Light intensities were quantitated using the IL 1350 Radiometer/Photometer, from International Light Inc., U.S.A.

D. Determination of Percentage of Apoptotic Cells

Percentage of apoptotic cells was determined by light microscopy on cytospin cell preparations stained with May-Grunwald-Giemsa. A total of 400 cells were counted by two individuals, independently, and the data are given as the average of the counts. Apoptotic cells were recognized by their smaller size and nuclei that were fragmented into condensed chromatin bodies.

E. Flow Cytometry Analysis

Cells harvested 5 hours after application of photodynamic stress were rinsed with phosphate buffered saline (PBS) and fixed with 70% aqueous ethanol. The cells were then resuspended in phosphate-citrate buffer (PC buffer) pH 7.8 (192 parts of 0.2 M $Na_2PHO_4$ and 8 parts of 0.1 M citric acid) at room temperature for 30 minutes and stained with propidium iodide in PC buffer containing 10 μg/ml RNase A. The cells were then analyzed in a Coulter EPICS XL-MCL flow cytometer with the entire field gated to include the various changes that affected the cells.

F. DNA Fragmentation Assay

DNA fragmentation in cells undergoing apoptosis was assayed as described previously (Lotem, J. and Sachs, L., *Cell Growth and Differ.*, 6, 647–653 (1995). $2 \times 10^6$ cells pelleted in Eppendorf tubes were lysed in 0.5 ml lysis buffer containing 10 mm Tris-HCl, pH 7.5, 0.6% SDS, 10 mM EDTA and 15 µg/ml RNA mixture (Ambion Corp., Austin Tex.). After incubation at 37° C. for 10 minutes, NaCl was added to 1 M and the mixture was kept overnight at 4° C. The preparation was spun at 14,000 g for 30 minutes at 4° C., the supernatant collected, phenol extracted and DNA precipitated overnight at −20° C. by adding 1 ml ethanol. The DNA pellet was air-dried, dissolved in 20 µl TE buffer (10 mM Tris, 10 mM EDTA, pH 7.5) at 4° C. for 24 hours, electrophoresed for 4 hours at 2 V/cm in 1.5% agarose gel containing 0.5 µg/ml ethidium bromide and photographed under U.V. light.

Example 1

Killing of Malignant Tumor Cells in Culture by Dimethyl-TMH and TMH in the Dark

Three human malignant cell lines were evaluated to sensitivity to dimethyl TMH in vitro. Human U251 glioblastoma, U87MG glioblastoma and LAN5 neuroblastoma cells were plated ($2 \times 10^5$ per well) in 96-well flat bottom microculture plates, treated with dimethyl-TMH and hypericin at dose ranges of 0 (control), 0.1–20 µM in complete darkness for a period of 72 hours. The medium was aspirated, the adherent monolayer was washed with phosphate-buffered saline, and cell viability was monitored by the MTI assay.

Figure 2:
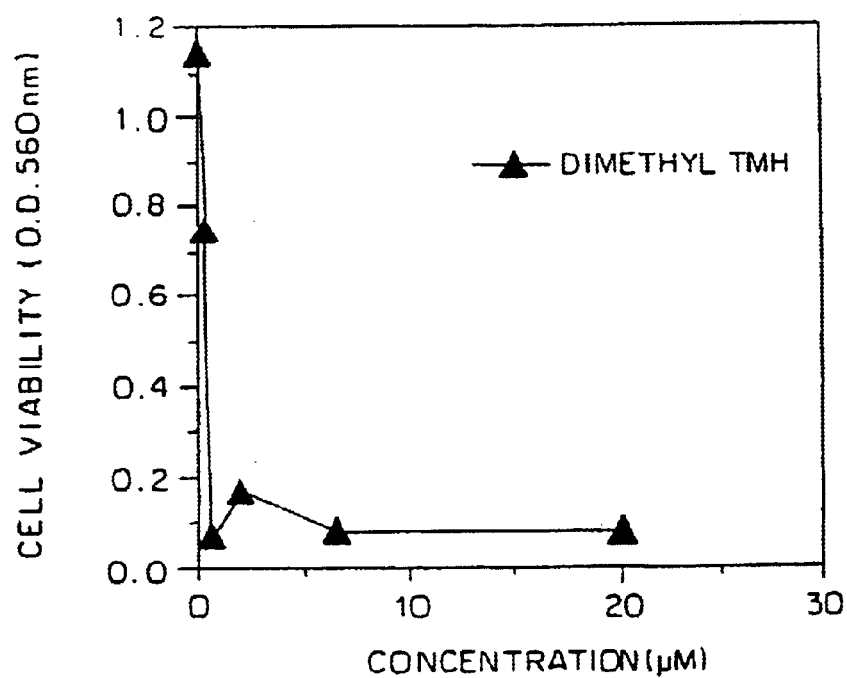
FIG. 2 shows the effects of various concentrations of dimethyl TMH on LAN5 neuroblastoma cell viability in complete darkness.
Figure 3:
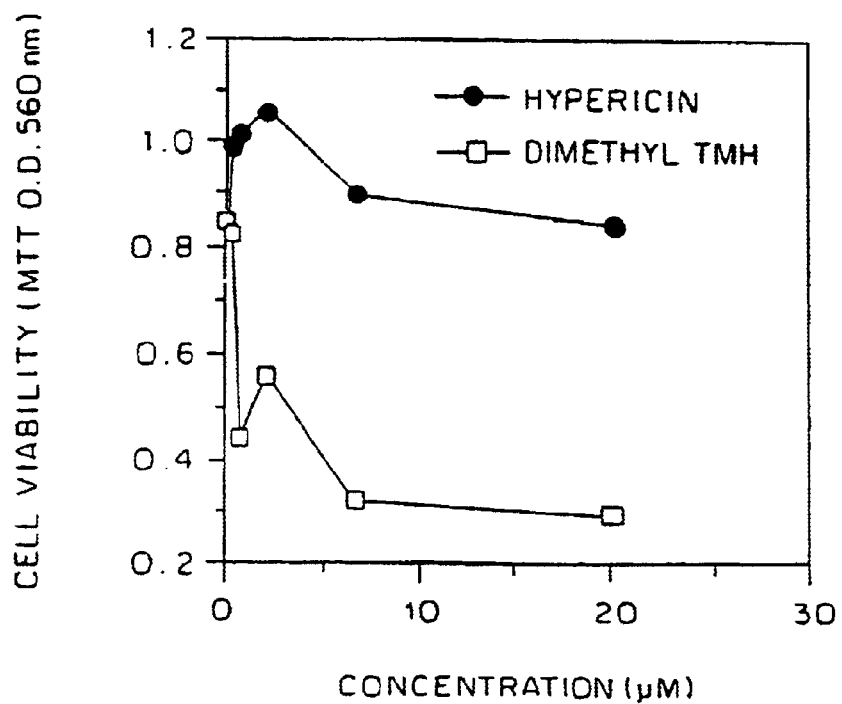
FIG. 3 shows the effects of various concentrations of dimethyl TMH and hypericin on U87MG glioblastoma cell viability in complete darkness.

FIGS. 1, 2 and 3 show the results for the U251 glioblastoma, LAN5 neuroblastoma and U87MG glioblastoma cells, respectively, comparison of the cytotoxic activity with hypericin being shown in FIGS. 1 and 3. Cell viability was lost in all thee after exposure to dimethyl-TMH for at least 72 hours, as measured in MTF viability assays. Loss of cell viability following treatment with dimethyl-TMH in the dark of the two glioblastoma cells was more effective than the treatment with hypericin.

Figure 4:
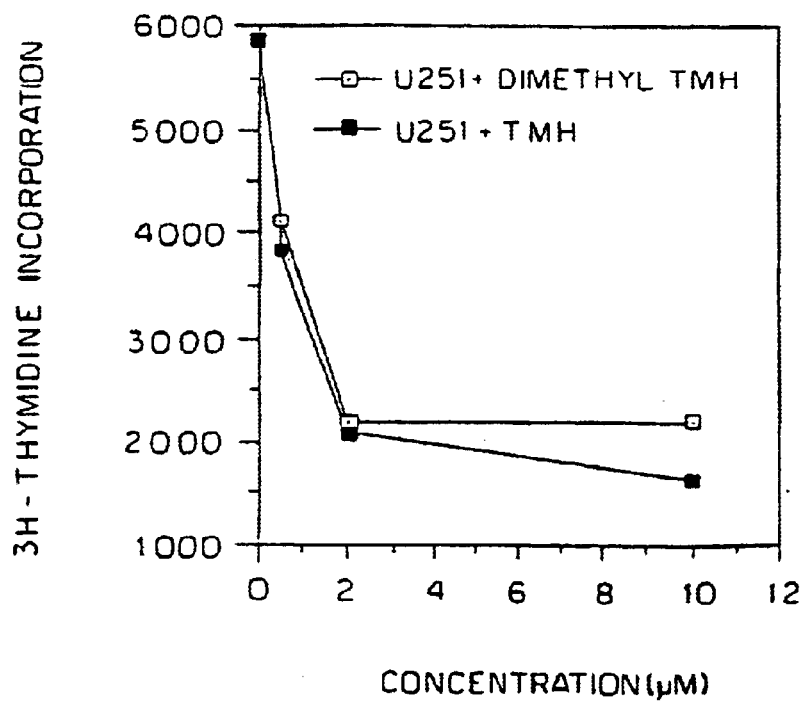
FIG. 4 shows the effects of various concentrations of dimethyl TMH and TMH on U87MG glioblastoma cell viability in complete darkness for 48 hours.

The experiment was then repeated with U251 glioblastoma cells treated with dimethyl-TMH or tetramethoxyhelianthrone (TMH) at dose ranges of 0.1–12 µM in complete darkness. Cell viability was monitored by the MTT assay. The results, in FIG. 4, show that both dimethyl-TMH and TMH exhibited comparable cytotoxic activities to U251 cells.

Example 2

Figure 5:
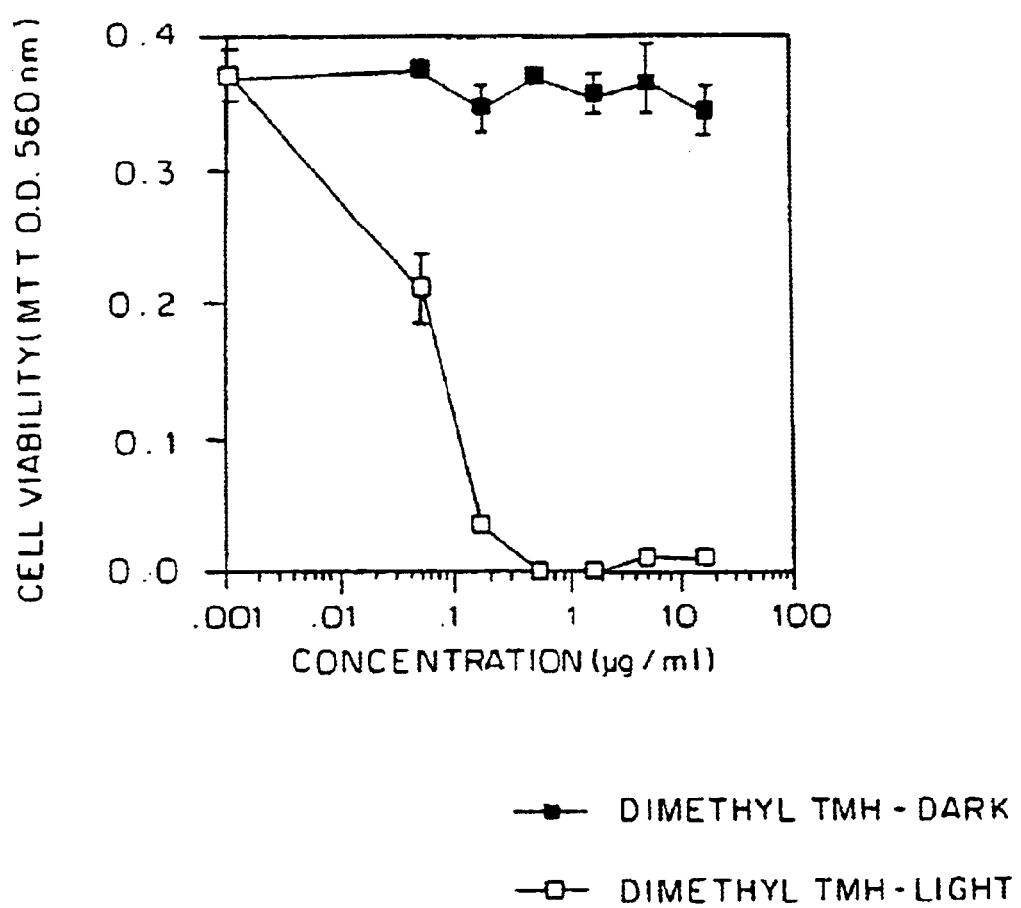
FIG. 5 shows the light-dependent photodynamic effects of dimethyl TMH on primary post-mitotic human peripheral blood lymphocytes (PBL) viability in the dark and in conjunction with light.

Light-dependent, Photodynamic Effects of Dimethyl-TMH on Normal Primary Human Peripheral Blood Lymphocytes Human peripheral blood lymphocytes (PBL) are non-proliferating cells in the absence of mitogenic stimuli. The effects of different doses of dimethyl-TMH on PBL were examined in the presence or absence of irradiation with polychromatic white light. PBL (post-mitotic) were plated ($2 \times 10^5$ cells/well) in two separate round bottom 96-well plates (in triplicates). Dimethyl-TMH was added to the cultures. One plate was kept in the dark, and the other was exposed to polychromatic white light at a fluence rate of 8 mW/cm$^2$ for 30 min (a total of 14.4 J/cm$^2$). Both plates were then cultured at 37° C., 5% $CO_2$ for 72 hours and cell viability was assayed by the MTT assay. The results, in FIG. 5, show that dimethyl-TMH had no effect on PBL viability in the absence of light irradiation, however, photosensitization with light caused cell death with an $LD_{50}$ of approximately 0.65 µM dimethyl TMH, indicating that dimethyl-TMH is a potent photodynamic reagent but does not act on non-proliferating cells in the absence of light irradiation.

Example 3

Determination of the Cell Cycle Phases in which Dimethyl-TMH Arrests Malignant Tumor Cells Growth and Proliferation in the Dark Cell cycle and DNA content analyses were conducted in U251 human glioblastoma cells after treatment with 5 µg/ml (10 µM) dimethyl-TMH for 24, 48 and 72 hours, and on LAN5 neuroblastoma cells after 48 hours. The cells were then stained with propidium iodide, washed with PBS and analyzed in a fluorescence activated cell sorter (FACS). A computer program arranged the DNA-related fluorescence as follows: the minimal amount of fluorescence is considered to be one whole set of cellular DNA related to the resting $G_1$ phase. A double amount of fluorescence is considered to be $G_2$ phase, in which the whole genome is duplicated following complete DNA synthesis, and the in-between amounts are considered to be the DNA synthetic S-phase, in which the total DNA synthesis is not yet completed.

Figure 6A:
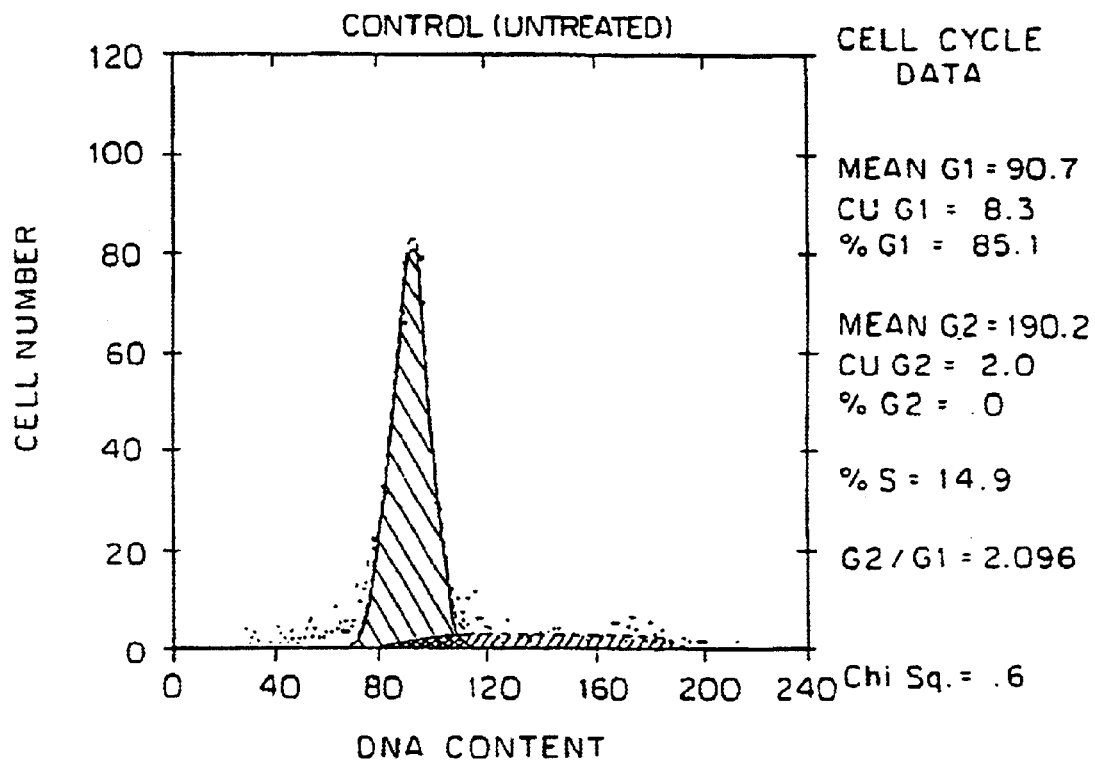
FIGS. 6A–D show the effects of 10 $\mu$M dimethyl TMH on U251 human glioblastoma cells in culture without (6A) and after treatment for 24 hours (6B), 48 hours (6C), and 72 hours (6D).
Figure 6B:
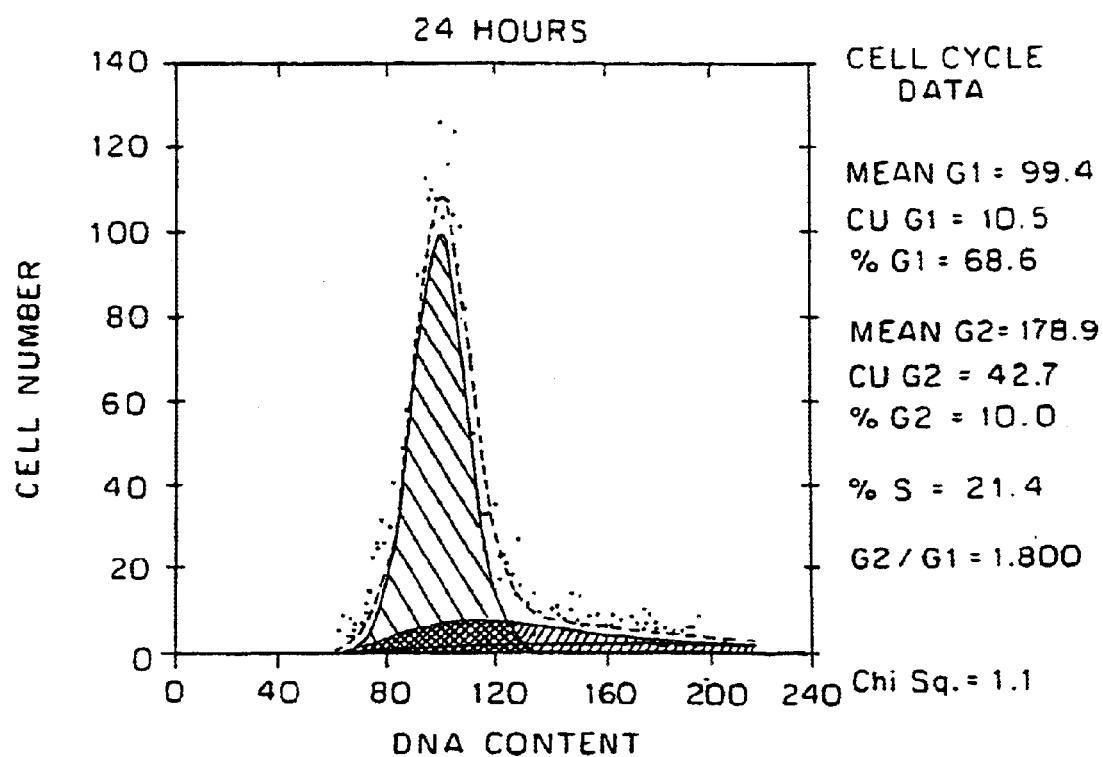
Figure 6:
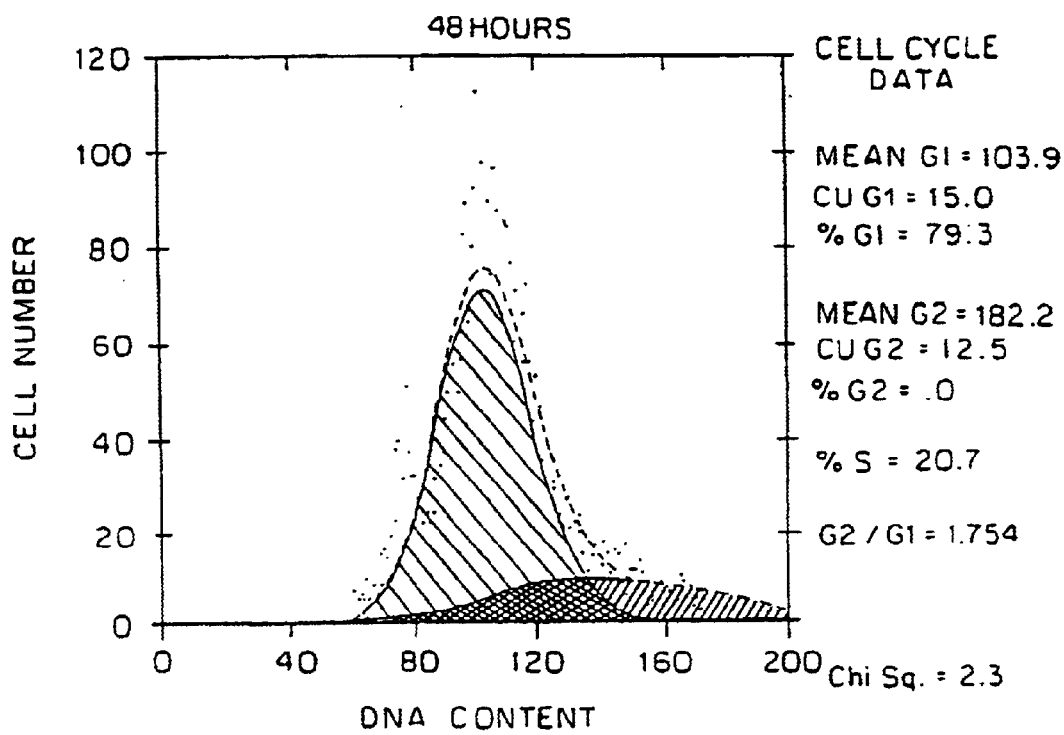
Figure 6D:
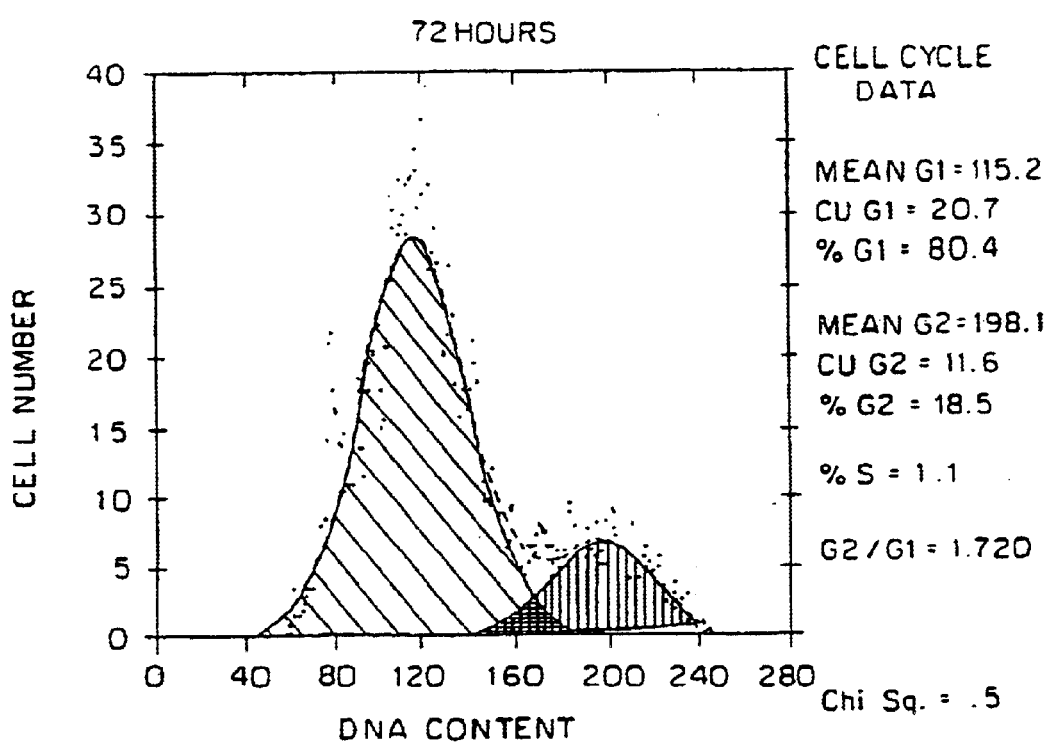
Figure 7A:
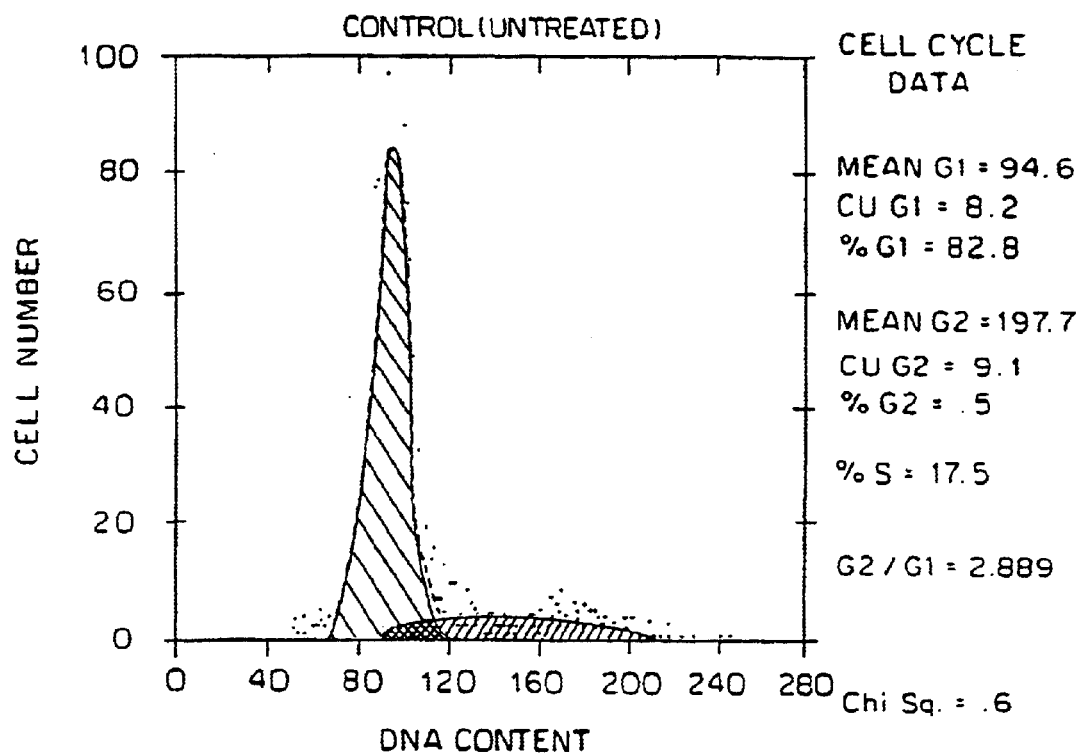
FIGS. 7A–C show the dose response effects of 10 $\mu$M (7B) and 20 $\mu$M (7C) dimethyl TMH on U251 human glioblastoma cells in culture. Control (untreated, 7A).
Figure 7B:
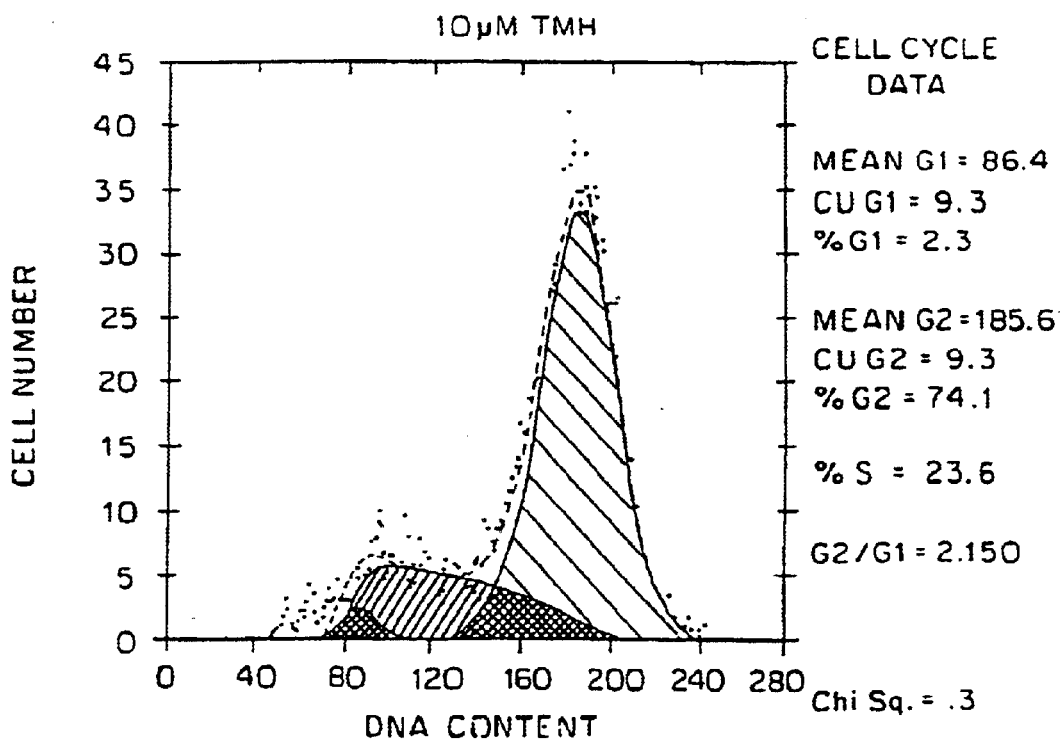
Figure 7C:
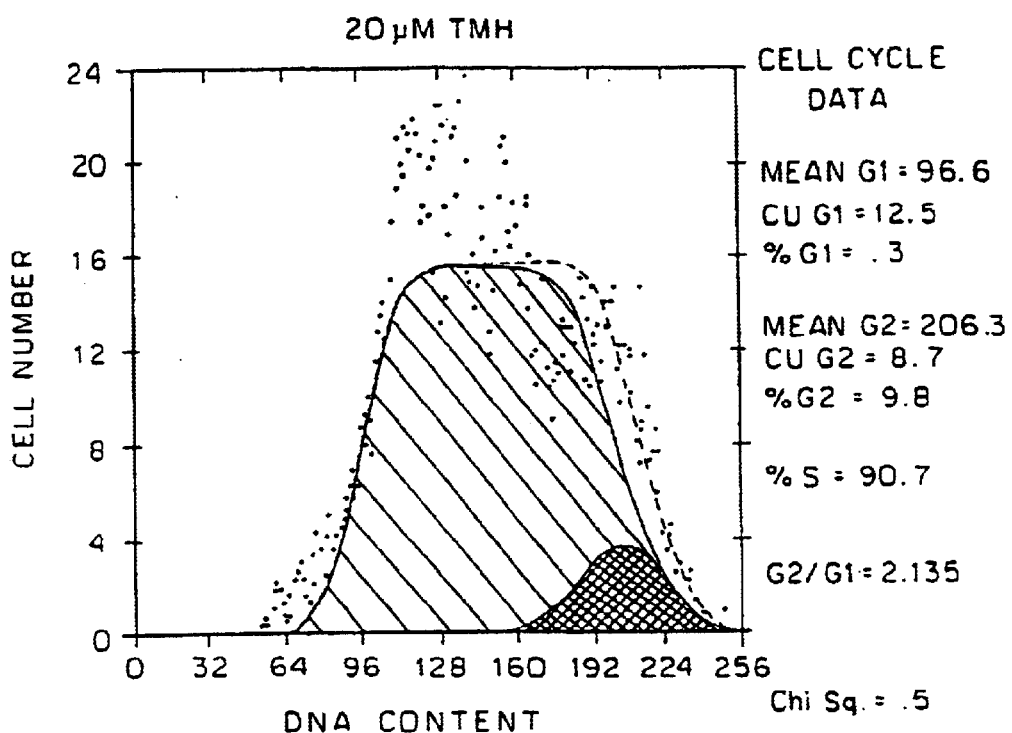

The results, shown in FIGS. 6–7, reveal that administration of 10 µM dimethyl-TMH to U251 human glioblastoma cells produced cell proliferation arrest at mid-S phase (12 B). The proportion of cells found in the S-phase increased steadily with the duration of exposure to dimethyl-TMH (FIGS. 6A, 6B, 6C). When the dose of dimethyl-TMH was increased from 10 µM to 20 µM (FIGS. 7B, 7C), an exclusive arrest at the S phase occurred. Fluorescence in situ hybridization (FISH) studies confirmed this imbalance in DNA replication at the gene level. This cell cycle arrest causes the toxic effects which elicits cell death.

Example 4

Prevention of Formation of Metastases in BALB/c Mice Bearing Highly Invasive Squamous Cell Carcinoma with dimethyl tetramethoxyhelianthrone The effective cytocidal activity of dimethyl-TMH in vitro encouraged the evaluation of its safety and anti-tumoral efficacy profile in tumor-bearing mice. Experiments were carried out in mice bearing tumors derived from the SQ2 highly metastatic anaplastic squamous cell carcinoma (SCC) line. This tumor develops as multifocal centers that spread at the vicinity of the primary tumor and metastases develop approximately two months after cell inoculation. Treatments with 300–600 µM dimethyl-TMH/mouse, administered twice or three-times a week were initiated when the tumors reached 5–7 mm in diameter.

Table 1 shows the results of one of the experiments, in which BALB/c mice were inoculated with $5 \times 10^5$ cells of the SQ2 anaplastic squamous cell carcinoma line, intradermally in shaved backs, 8 mice per group. When the primary tumors reached a diameter of 5 mm, therapy with 300 µM dimethyl-TMH/mouse, administered intraperitoneally twice per week, was initiated. Three weeks after the initiation of therapy, the number of tumor foci, which have developed at the primary tumor site, was recorded. The number of foci, which developed 21 days after start of therapy, was considerably reduced by dimethyl-TMH administered at therapeutic doses that were non-toxic to the animals. In addition to preventing the multifocal spread of this tumor, the primary tumors hardened and fell off in 5 of the treated mice, indicating that complete cure of this tumor may be achieved once treatment regimens are optimized.

TABLE 1

The Number of Tumor Foci observed 21 days after the Start of Therapy with Dimethyl-TMH

| Mice | 1 focus | 2 foci | 3 foci | 4 foci |
|---|---|---|---|---|
| Control | 3 | 0 | 2 | 5 |
| Dimethyl.-TMH | 8 | 1 | 0 | 0 |

Example 5

Survival of Squamous Cell Carcinoma-Bearing Mice Treated with Dimethyl-TMH

Figure 8:
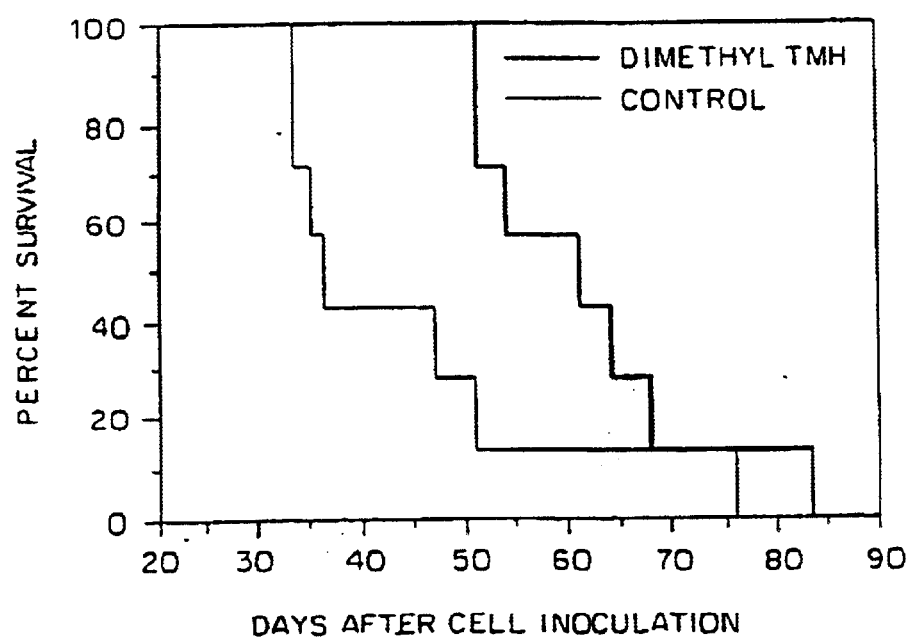
FIG. 8 shows percent survival of BALB/c mice inoculated with squamous cell carcinoma cells after treatment with dimethyl TMH.

In another experiment, BALB/c mice were inoculated with $5\times10^5$ cells of the SQ2 highly metastatic anaplastic squamous cell carcinoma line, intradermally in shaved backs. When the primary tumors reached a diameter of 3–4 mm, i.p. administration of dimethyl TMH 200 µg/mouse (400 µM/mouse) was initiated on day 7 after tumor cell inoculation and then administered twice weekly to the tumor-bearing mice 2× per week for six weeks (total of 12 doses). Animal survival was then followed. The results in FIG. 8 show that animal survival was prolonged by approximately 40.3% compared to untreated controls. It is noteworthy that the primary tumors continued to grow during the treatment and nevertheless animal survival was prolonged. This appears to be the result of reduced metastatic growth as evident from Table 1 in Example 4 above.

Example 6

The Utilization of dimethyl TMH in Antineoplastic Therapy of Malignant Tumors in Mice The antineoplastic effects of dimethyl TMH in vivo can be examined in a number of murine experimental tumors. These include Esb murine lymphoma, MCA-105 sarcoma and B16 melanoma which are evaluated in C57BL/6J mice. DA3$^{hi}$ murine breast carcinoma cells, a highly metastatic variant of DA3, which generates metastatic breast adenocarcinoma in BALB/c mice, and A431 cells which generate epidermoid tumors in NIH Swiss mice, are evaluated for sensitivities to treatment with dimethyl TMH or with TMH. Tumors are propagated in mice, 8–10 animals per group, by intradermal inoculations of tumor generating cells. Dimethyl TMH dose escalations ranging between 20–1000 µM (10–500 µg/mouse) are examined. Frequencies of administrations are varied from daily administrations, 3× weekly to 1× weekly, administered for periods ranging from 2–12 weeks. Animals are monitored for differences in primary tumor size compared to untreated tumor bearing control mice. To analyze for spread of metastases all mice are sacrificed at the death of the first control group mouse or at times designated for termination of the experiment. Endpoints used in previous examples are applied. Spleen, liver and lung weights are parameters which we use for determination of metastatic load. Total number of metastatic foci in each of these organs is a second parameter determined after fixation in Bouins solution. Animal survival is another endpoint that is examined. The mean and median survival times, after tumor cell inoculation, is determined. The significance of prolongation of survival is calculated by comparison to controls of untreated tumor bearing animals without exposure to light (compound's dark effects), in the Paired Student's t-test.

In one experiment, the anti tumoral activity of dimethyl TMH to human tumors in an in vivo model is evaluated in the C.B-17 SCID mouse strain (Fox Chase). Human epidermoid and glioblastoma tumors have been induced in the skin of these mice by inoculation with the corresponding human cell lines. The animals are then subjected to various dimethyl TMH treatment protocols, the compound administered intraperitoneally. The animals are monitored for tumor size and for survival.

Example 7

Prevention of Formation of Metastases in DA-3$^{HI}$ Induced Breast Adenocarcinoma Tumors in BALB/c Mice with Hypericin The primary tumor size at which metastases occur in DA-3$^{HI}$-derived breast adenocarcinoma tumors was initially calibrated in BALB/c mice inoculated with $5\times10^5$ DA-3$^{HI}$ tumor cells intradermally. It was found that if surgical removal of the primary tumors was performed when tumors reached a diameter of 5 mm or less, the resection of the primary tumor cured the mice. If the resection was performed on tumors with larger diameters, the mice died of metastases. A diameter of approximately 5 mm appears to be the cutoff at which metastases begin to spread.

Figure 9A:
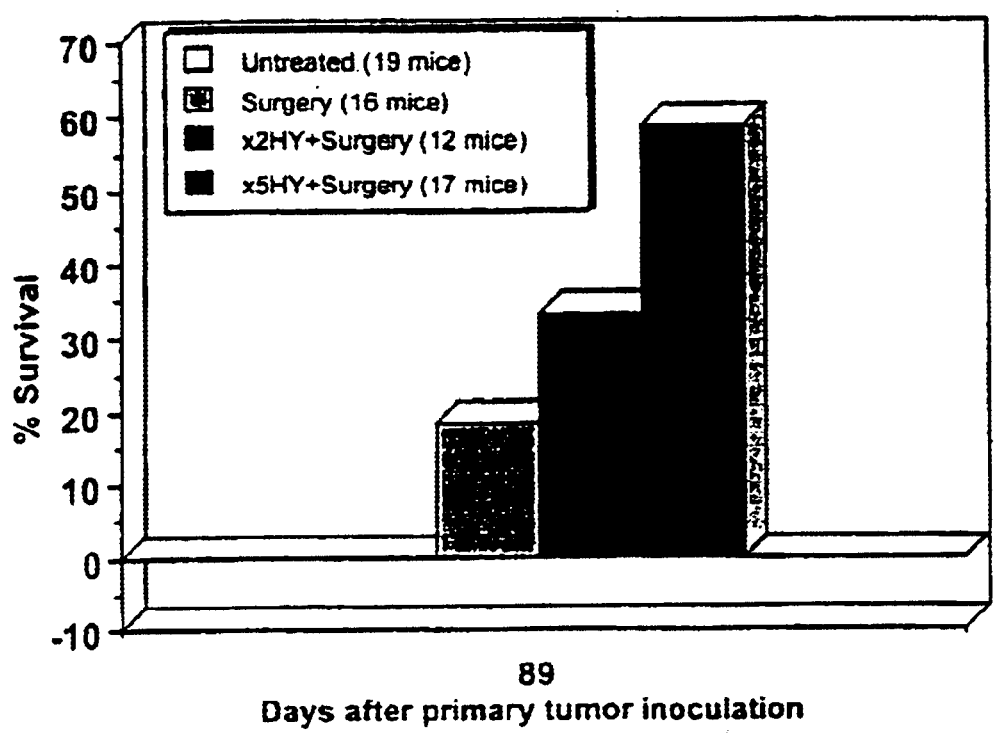
FIGS. 9A–B show percent survival of BALB/c mice inoculated with DA-3$^{HI}$-induced breast adenocarcinoma cells after treatment with hypericin, at days 89 (9A) and 100 (9B) after surgery.

DA-3$^{HI}$ tumors were induced in 12-week old female BALB/c mice as described above. When the tumors reached diameters of 8–10 mm the mice were divided into four groups. One group of 19 mice was left untreated and in the three other groups the tumors were surgically removed. One of the resected groups received two intraperitoneal (i.p.) injections with 200 µg hypericin (HY) each 5 days apart beginning two days prior to surgery (16 mice). Another resected group received five i.p. injections with 200 µg hypericin each, 5 days apart beginning two days prior to surgery (17 mice). One resected group was not treated with hypericin (16 mice). The mice were then followed for survival. FIG. 9A shows that none of the tumor-bearing untreated mice survived and 20% of the mice that underwent surgery also survived at day 89. However, administration of 2 i.p. injections of hypericin increased the survival rate to 35% and administration of 5 hypericin doses increased the survival rate to 60%.

Figure 9B:
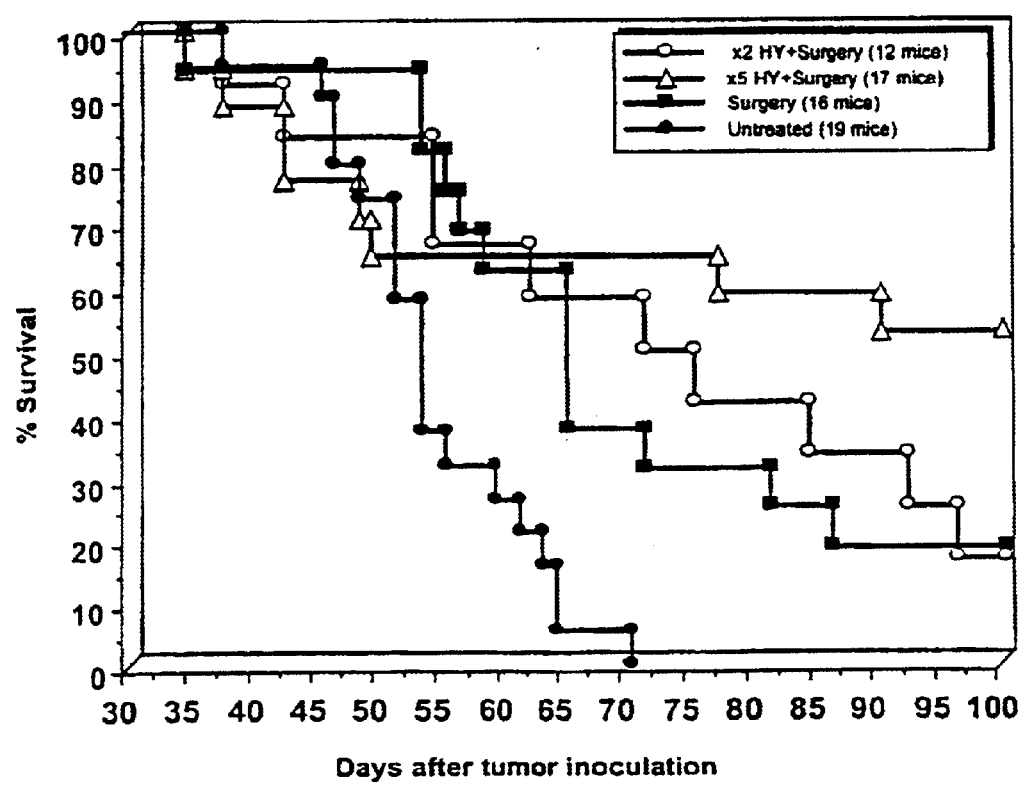

FIG. 9B shows the cumulative survival of mice which received 2 and 5 doses of hypericin (200 µg/mouse each) through 100 days following surgery (these values persisted for 164 days after tumor inoculation). They suggest complete prevention of metastases in the surviving group of mice, particularly in the group which received five doses of hypericin. These results indicate that hypericin protects the mice from developing metastases and thus, prevents animal death form the outcome of systemic dissemination of cells from the primary tumor.

Example 8

Prevention of Formation of Metastases in BALB/c Mice Bearing Highly Invasive Squamous Cell Carcinoma with Hypericin In another set of experiments squamous cell carcinoma tumors were generated in BALB/c mice by inoculating $5\times10^5$ SQ2 cells per mouse. When the tumors reached a diameter of 1.0–1.2 cm in diameter they were removed by surgery (resected). One group of 5 mice also received three i.p injections of hypericin of 100 µg/mouse prior to surgery and two regimens of 50 µg/mouse post surgery at intervals of 5 days between each dosing. Another group of 8 mice received six hypericin i.p. injections of 100 μg/mouse prior to surgery and five regimens of 50 μg/mouse post surgery at intervals 5 days apart. One control group of 17 mice underwent surgery only without treatments with hypericin and another control group remained untreated (22 mice). Animal survival was then followed. It was then found that 60% of the mice which received three hypericin injections remained alive beyond 240 days following tumor cell inoculation; of the mice receiving 6 hypericin injections 40% remained alive, whereas of the mice which underwent surgery only, 20% remained alive. These results also show protection rates of 20–40% due to hypericin administration.

In an effort to understand how hypericin prevents the growth of metastases the experiment was repeated and the morphology of the metastatic lesions then followed. Primary DA-3$^{HI}$ tumors were induced in BALB/c mice. Surgery was conducted on the tumors when diameters reached 8–10 mm. These mice (17 animals) were divided into two groups, one treated with 5 doses of hypericin 200 μg/mouse at 5 day intervals as previously described (9 animals) and another group served as untreated control (8 mice). The animals were grown for two more months. The mice were then sacrificed and the internal organs examined for metastatic lesions. The physical examination revealed numerous well developed metastatic lesions in untreated mice that were supplied with large visible blood vessels. The few lesions that did develop in some of the mice treated with hypericin were much smaller, somewhat more necrotic and devoid of such vasculature (supplying blood vessels). This was evident only when hypericin injections were initiated very early prior to the resection of the primary tumor. These observations indicate that hypericin inhibits angiogenesis (growth of new vasculature). It is likely that this lack of blood supply prevented the development of metastases and not any direct anti-cancer effects. Since angiogenesis is primarily mediated by vascular endothelium growth factor (VEGF), hypericin may interfere with either the formation or secretion of VEGF from tumor cells or with its targeting of growth inducing receptors on vascular endothelial cells. Without wishing to be bound to any proposed mechanism, hypericin has been shown to inhibit protein kinase C and the latter is essential in VEGF production. Interference with the signal transduction pathway that culminates in the production of VEGF might be the mechanism for hypericin or helianthrone derivative-mediated inhibition of the VEGF effect that results in inhibition of metastatic lesion growth. Irrespective of the proposed mechanism of action it is now demonstrated that these compositions are highly potent inhibitors of angiogenesis.

Example 9

Figure 10A:
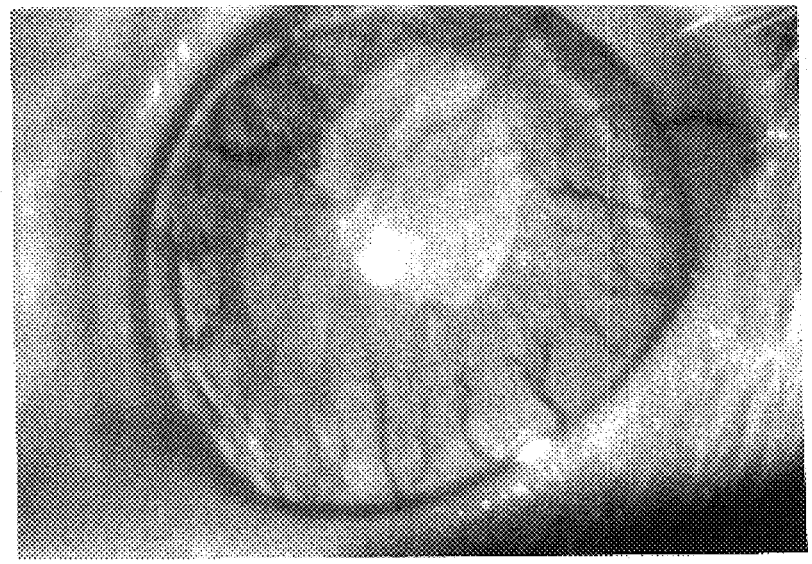
FIGS. 10A–B are photographs of eyes of rats after heparanase-induced angiogenesis with no treatment (10A, control) and after treatment with hypericin (10B).
Figure 10B:
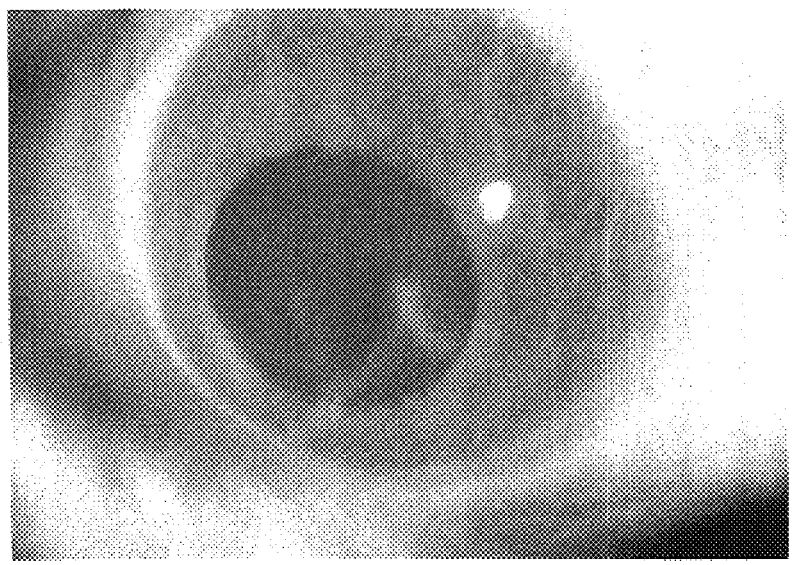

Prevention of Vascularization (Angiogenesis) of the Anterior Chamber of the Eye by Systemic Administration of Hypericin Four rats (250 g each) were given three intraperitoneal injections of hypericin (750 μg per dose in 5 ml water containing 3.5% ethanol) at four day intervals. The following day the animals were anesthetized with xylazine-ketamine and angiogenesis (formation of new blood vessels) was induced by inoculating 2 μl heparanase (30 μg/ml) into the frontal compartment of the eye in the cornea of one of the two eyes in each rat. A fourth intraperitoneal injections of 750 μg hypericin was applied the next day. Two positive control animals received only 2 μl heparanase (30 μg/ml) into the frontal compartment of the eye. Angiogenesis was then allowed to develop for 5 days at which time animals were anesthetized with xylazine-ketamine and examined and photographed under a binocular microscope for development of blood vessels in the anterior chamber of the eye. The photograph in FIG. 10A shows the blood vessels in a control eye of a rat after heparanase-induced angiogenesis and no treatment with hypericin while the photograph in FIG. 10B shows the absence of blood vessels in the eye of a hypericin-treated rat. Similar protection was obtained when angiogenesis was induced in rat eyes with bFGF (basic fibroblast growth factor) (not shown).

Example 10

Hypericin Interferes with Angiogenesis

Rat aorta is carved into rings which are embedded in fibrin gels and cultured in MCDB 131 medium. Endothelial cells that detach from the aorta rings generate branching microvessels according to a method previously described (Nicosia R. F. and Ottinetti A. Growth of microvessels in serum-free matrix culture of rat aorta. Laboratory Investigation 63: 115, 1990). Addition of hypericin at a dose range of between 0.1–10 μg/ml (0.2–20 μM), or dimethyl tetrahydroxyhelianthrone at a dose range of between 0.1–10 μg/ml (0.2–20 μM) results in the inhibition of formation of the organized microvessels.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

REFERENCES

Couldwell W. T., R. Gopalakrishna, D. R. Hinton, S. He, M. H. Weiss, R. E. Law, M. L. Apuzzo and R. E. Law. Hypericin: a potential antiglioma therapy. Neurosurgery 35:705–710, 1994.

Diwu Z., Zimmermann J., Meyer Th., & Lawn J. W. Design, synthesis, and investigation of mechanisms of action of novel protein kinase C inhibitors: perylene quinonoid pigments. Biochem. Pharmacol. 47; 373–385,1994.

Folkman J.: Angiogenesis and its inhibitors. In: Important Advances in Oncology. De Vita V T, Hellman S, Rosenberg S A—Editors. p 42. Philadelphia, Lippincott Co., 1985.

Folkman J. Watson K., Ingber D., Hanahan D. Induction of angiogenesis during the transition from hyperplasia to neoplasia. Nature 339: 58, 1989.

Hadjur C., Jeunet A. and Jardon P. Photosensitization by hypericin: ESR evidence for singlet oxygen and superoxide anion radicals formation in an in vitro model. J. Photochem. & Photobiol. B. Biol 26:67–74, 1994.

Hudson J. B., Lopez-Bazzocchi I. and Towers G. H. Antiviral activities of hypericin. Antiviral Res. 15:101, 1991.

Lavie G., F. Valentine, B. Levin, Y. Mazur, G. Gallo, D. Lavie, D. Weiner and D. Meruelo. Studies of the mechanisms of action of the antiretroviral agents hypericin and pseudohypericin. Proc. Nat. Acad. Sci.(USA) 86:5963, 1989.

Lavie G., Y. Mazur, D. Lavie and D. Meruelo. The chemical and biological properties of hypericin—A compound with a broad spectrum of biological activities. Medicinal Res. Rev. 15:111–119, 1994.

Lavie G., Mazur Y., Lavie D., Prince A. M., Pascual D., Liebes L., Levin B. and Meruelo D. Hypericin as an inactivator of infectious viruses in blood products. Transfusion 35: 392–400, 1995.

Losiewicz M. D., Bradley A. C., Kaur G., Sausville E. A. and Worland P. J. Potent inhibition of CDC2 kinase activity by the flavonoid L86-8275. Biochem. Biophys. Res. Commun. 201:589–595, 1994.

Meruelo D., G. Lavie, D. Lavie. Therapeutic agents with dramatic antiretroviral activity and little toxicity at effective doses: aromatic polycyclic diones hypericin and pseudohypericin. Proc. Nat. Acad. Sci.(USA) 85: 5230–5324, 1988.

Mossman T. Rapid colorimetric assay for cellular growth and survival: application to proliferation and cytotoxicity assays. J. Immunogen. 21:235, 1983.

Takahashi I. S. Nakanishi, E. Kobayashi, H. Nakano, K. Suzuki and T. Tamaoki. 1989. Hypericin and pseudohypericin specifically inhibit protein kinase C: possible relation to their antiretroviral activity. Biochem. Biophys. Res. Commun 165:1207.

Tang J., J. M. Colacino. S. H. Larsen and W. Spitzer. Virucidal activity of hypericin against enveloped and non-enveloped DNA and RNA viruses. Antiviral Res. 13:313–326, 1990.

What is claimed is:

1. A method for treating or inhibiting angiogenesis which comprises administering to a patient in need of such treatment a therapeutically effective amount of a compound of formula (I):

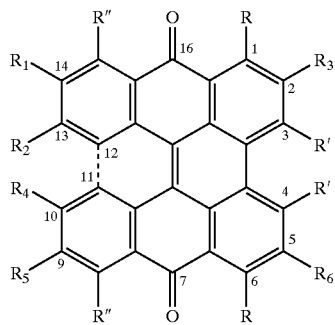

wherein the dotted line between positions 11 and 12 represent an optional C11–C12 bond; R is independently selected from the group consisting of hydroxy, $C_1$–$C_{10}$ alkoxy, NH—$C_1$–$C_{10}$ alkyl, and NH-hydroxy($C_1$–$C_{10}$)alkyl; R' is independently selected from the group consisting of hydroxy and $C_1$–$C_{10}$ alkoxy; R" is independently selected from the group consisting of hydrogen, hydroxy, $C_1$–$C_{10}$ alkoxy, NH—$C_1$–$C_{10}$ alkyl, and NH-hydroxy($C_1$–$C_{10}$)alkyl; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl, provided that R" is not hydrogen when there is a C11–C12 bond.

2. The method according to claim 1, where each R is the same and is selected from the group consisting of hydroxy, $C_1$–$C_{10}$ alkoxy, NH—$C_1$–$C_{10}$ alkyl, and NH-hydroxy($C_1$–$C_{10}$)alkyl; each R' is the same and is selected from the group consisting of hydroxy and $C_1$–$C_{10}$ alkoxy; each R" is the same and is selected from the group consisting of hydrogen, hydroxy, $C_1$–$C_{10}$ alkoxy, NH—$C_1$–$C_{10}$ alkyl, and NH-hydroxy($C_1$–$C_{10}$)alkyl.

3. The method according to claim 1, wherein each R" is hydrogen when there is no C11–C12 bond.

4. The method according to claim 3, wherein each R" is selected from the group consisting of hydroxy, $C_1$–$C_{10}$ alkoxy, NH—$C_1$–$C_{10}$ alkyl, and NH-hydroxy($C_1$–$C_{10}$)alkyl.

5. The method according to claim 1, wherein each R or each R" is hydroxy or methoxy.

6. The method according to claim 5, wherein R and R" are hydroxy or methoxy.

7. The method according to claim 1, wherein the compound of formula I to be administered is selected from the group consisting of:

hypericin;
10,13-dimethyl-1,3,4,6-tetramethoxyhelianthrone,
1,3,4,6-tetrahydroxyhelianthrone,
1,3,4,6-tetramethoxyhelianthrone,
10,13-dimethyl-1,3,4,6-tetrahydroxyhelianthrone,
10,13-di(methoxycarbonyl)-1,3,4,6-tetramethoxyhelianthrone,
1,6-di-N-butylamino-3,4-dimethoxy-helianthrone,
1,6-di-N-butylamino-3,4-dimethoxy-10,13-dimethyl-helianthrone,
1,6-di-(N-hydroxyethylamino)-3,4-dimethoxy-helianthrone,
2,5-dibromo-1,3,4,6-tetrahydroxyhelianthrone, and
2,5-dibromo-10,13-dimethyl-1,3,4,6-tetrahydroxyhelianthrone.

8. The method according to claim 1, wherein the compound is administered with a carrier and in an amount of between about 0.1 micrograms and 1 mg per kg of patient body weight in a regimen of one of more times per day.

9. The method according to claim 1, wherein the patient is treated with an amount and regimen of the compound for inhibition of tumor metastases.

10. The method according to claim 9, wherein the treatment is carried out in the absence of light irradiation.

11. The method according to claim 1, wherein the patient is treated with an amount and regimen of the compound for inhibition of an angiogenesis-associated ophthalmologic disorder.

12. The method according to claim 11, wherein the angiogenesis-associated ophthalmologic disorder is diabetic retinopathy, macular degeneration, or eye infection.

13. The method according to claim 1, wherein the patient is treated with an amount and regimen of the compound for inhibition of restenosis.

* * * * *

UNITED STATES PATENT AND TRADEMARK OFFICE
CERTIFICATE OF CORRECTION

PATENT NO.   : 6,867,235 B2
DATED        : March 15, 2005
INVENTOR(S)  : Mazur et al.

It is certified that error appears in the above-identified patent and that said Letters Patent is hereby corrected as shown below:

Column 3,
Lines 27-41, delete formula (I) and insert the following:

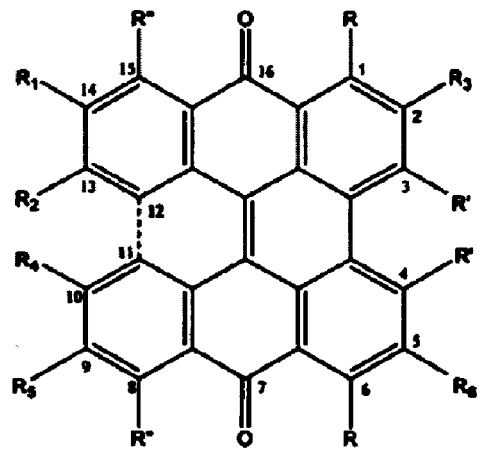

Column 17,
Lines 33-46, delete formula (I) and insert the following:

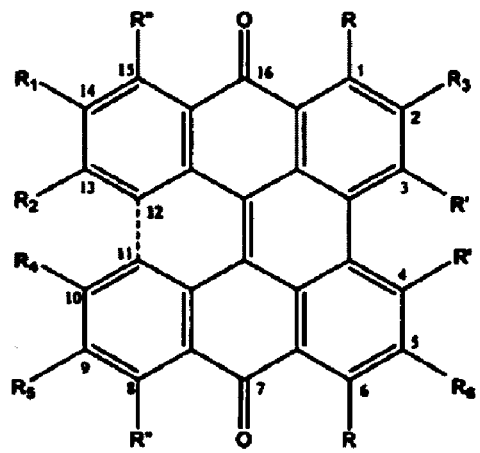

UNITED STATES PATENT AND TRADEMARK OFFICE
CERTIFICATE OF CORRECTION

PATENT NO.   : 6,867,235 B2
DATED        : March 15, 2005
INVENTOR(S)  : Mazur et al.

It is certified that error appears in the above-identified patent and that said Letters Patent is hereby corrected as shown below:

Column 18,
Line 42, after "body weight in a regimen of one" delete "of" and insert -- or --.

Signed and Sealed this

Twenty-fifth Day of October, 2005

JON W. DUDAS
*Director of the United States Patent and Trademark Office*